United States Patent [19]
Chen

[11] Patent Number: 5,370,900
[45] Date of Patent: Dec. 6, 1994

[54] THIN-FINGERED MEDICAL GLOVE

[75] Inventor: Mao-Ching Chen, Arlington, Tex.

[73] Assignee: Johnson & Johnson Medical, Inc., Arlington, Tex.

[21] Appl. No.: 956,941

[22] Filed: Oct. 5, 1992

[51] Int. Cl.⁵ .............................. A01N 1/02
[52] U.S. Cl. .......................... 427/2.3; 2/168
[58] Field of Search ............... 427/2; 2/159, 163, 168; 264/134, 349

[56] References Cited

U.S. PATENT DOCUMENTS 1,908,719  5/1933  Willson .
2,097,528 11/1937  Morton ........................... 264/306
3,397,265  8/1968  Ansell ............................ 264/306

FOREIGN PATENT DOCUMENTS 1410097 12/1965 France .

Primary Examiner—Asok Pal
Assistant Examiner—P. Achutamurthy
Attorney, Agent, or Firm—James Riesenfeld

[57] ABSTRACT

A process for making medical gloves whose fingers have thinner walls than the rest of the gloves involves first depositing onto a hand-shaped glove form a layer of coagulant that comprises an ionic metal salt, then depositing an elastomeric layer. Part of the coated form is then leeched of metal ions in the coating, and the form is overcoated with a second elastomeric layer. The overcoated layer is thinner in the part where it overlies the leeched coating. The gloves find particular usefulness in delicate operations such as those performed by ophthalmologists.

9 Claims, 2 Drawing Sheets

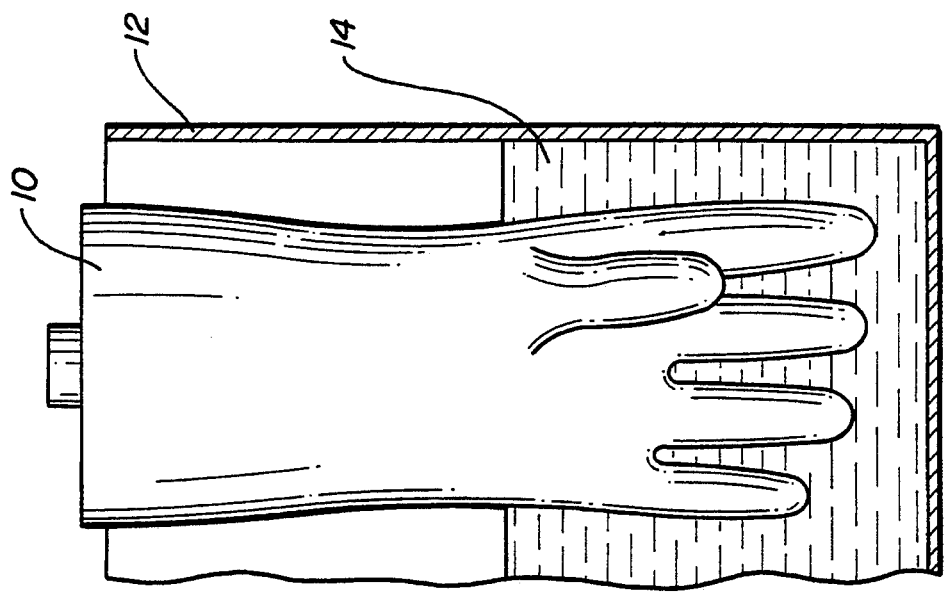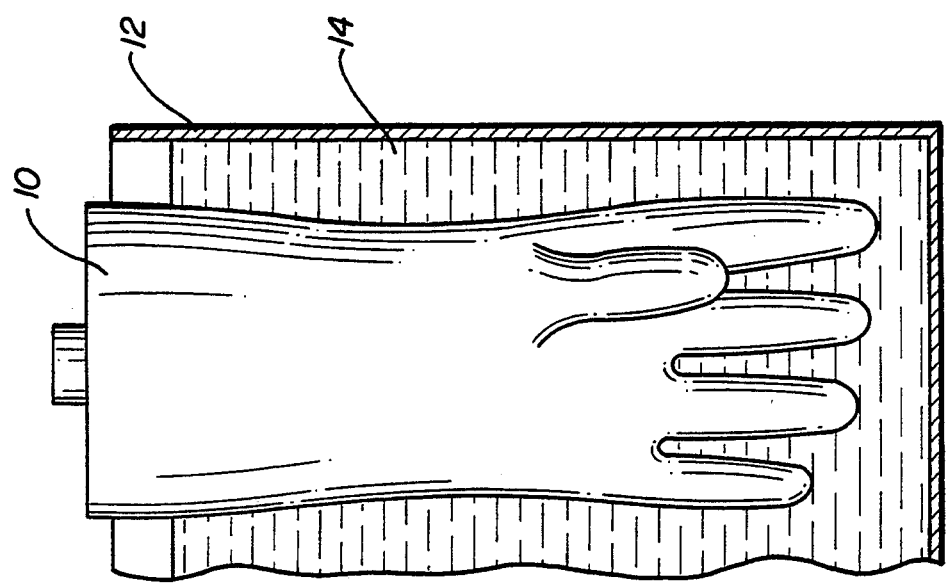

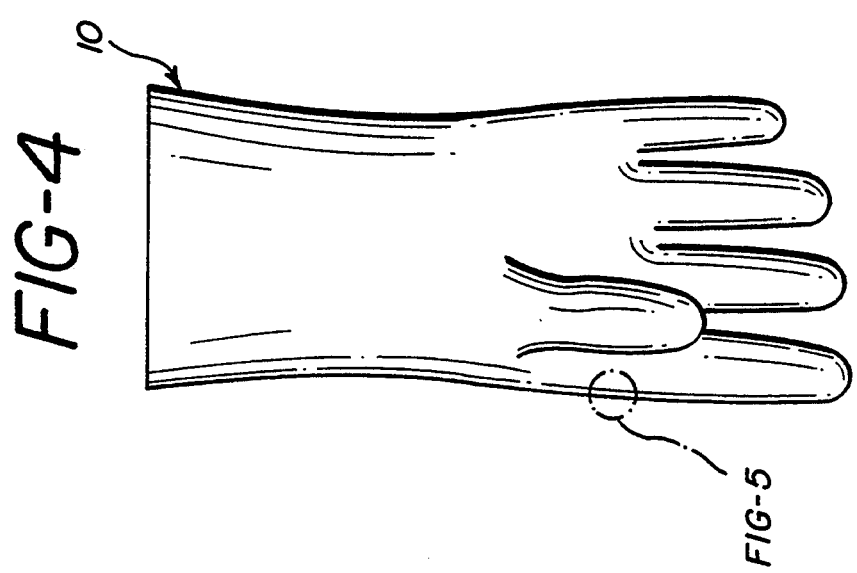
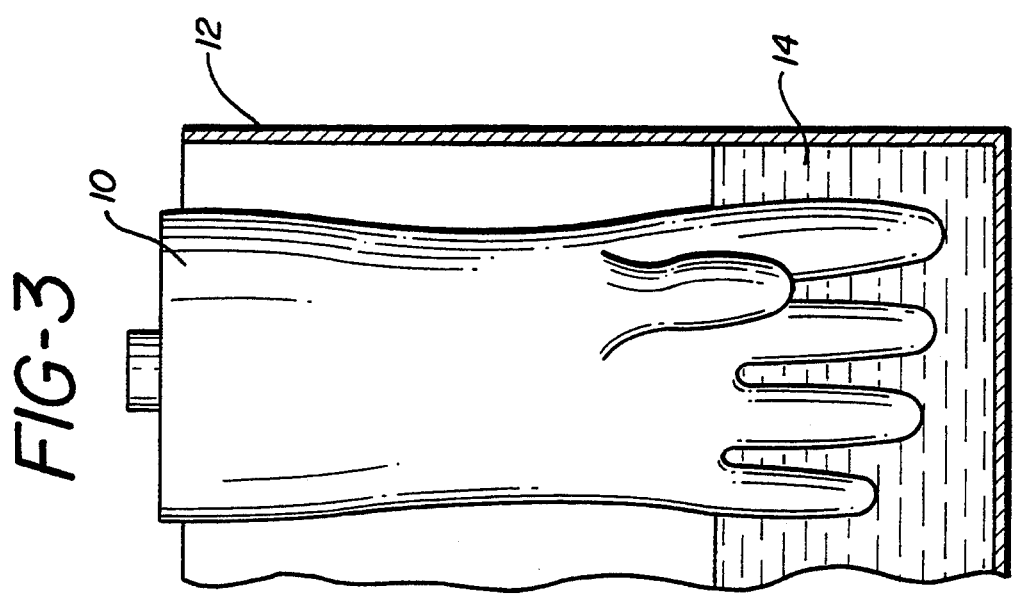

THIN-FINGERED MEDICAL GLOVE

BACKGROUND OF THE INVENTION

1. Field of the Invention

This invention relates to a process for making a medical glove whose fingers have thinner walls than the rest of the glove.

2. Description of the Related Art

Manufacturing surgical gloves involves a process that includes dipping a form fashioned to resemble the human hand into a solution of coagulant, drying the coagulant and then immersing the form into an elastomeric (e.g., latex) compound. After depositing the layer of latex compound on the form, the forms are usually rotated continuously until the coagulant reacts producing a gelled latex film. This rotation equalizes any wet latex runs and assures a more uniform overall gauge in the finished gloves. After the film is gelled, it is leached with water in order to remove any water soluble materials from the deposited film, dried, vulcanized and stripped from the glove form resulting in a finished glove. The above process involves dipping the glove form into a latex compound fingertips first; thus the fingertips are the last to be pulled out of the latex compound. Therefore, the fingertip gauge of the glove produced with the above process must be heavier than or equal to the cuff gauge. To prevent cuff tears during donning, the cuff gauge of a glove is generally at least 0.15 mm. Consequently, the fingertip gauge must be equal to or thicker than 0.15 mm. By these standards, current gloves are not suitable for delicate operations, such as those performed by ophthalmologists, due to poor touch sensitivity. Various methods have been proposed to produce gloves in which the fingertip gauge is thinner than the cuff gauge.

U.S. Pat. No. 2,097,528, issued on Nov. 2, 1937, to H. A. Morton, discloses a method of making rubber gloves in which a glove form is first immersed in a coagulant solution to provide a uniform coating over the form. The form is then dipped into a neutralizing agent, fingers first, to a depth that corresponds to the portion of the glove on which a thinner deposit is desired. Neutralizing the coagulant reduces its effectiveness; thus, when the form is subsequently submerged in a latex dispersion, less latex is deposited on the neutralized coagulant and the resultant glove is thinner there. A similar result is achieved in a process in which the form is dipped in a latex solution two (or more) times, with a portion of the form being dipped into a neutralizing solution between latex immersions.

U.S. Pat. No. 3,397,265, issued on Aug. 13, 1968, to H. N. Ansell, discloses a process in which a glove form that is coated with a concentrated coagulant is immersed in a solvent for the coagulant to a depth that corresponds to the portion of the form on which a thin latex coating is ultimately desired. After removing the coagulant coating from that portion of the form, the form is dipped into a dilute coagulant, so that the dilute coagulant covers the portion of the form from which the concentrated coagulant had been removed. Finally, the form is immersed in a latex solution. More latex deposits on the portion of the form that is coated with concentrated coagulant than on the portion coated with dilute coagulant. Consequently, the resultant glove is thicker in the region of the cuff than in the fingers.

U.S. Pat. No. 3,859,410, issued on Jan. 7, 1975, to H. Sidley, discloses a method of reproducing a glove having relatively thin wall thickness in the finger and palm portions and thicker wall thickness in the cuff region by first spraying concentrated coagulant onto the cuff region of a form and dilute coagulant onto the fingers and palm. The form is then dipped in a latex solution, where a thicker latex coating deposits on the region coated with concentrated coagulant.

Each of the procedures of the prior art permit the fabrication of gloves having less thickness in the fingers than the cuff, but they involve the use of corrosive solvents and/or are unsuited for fabricating gloves having fingers of extremely thin (thickness <0.13 mm) wall thickness.

SUMMARY OF THE INVENTION

In accordance with the present invention, a process for making a medical glove comprises the steps of a) dip-coating onto a glove form a layer of coagulant that comprises an ionic metal salt, b) dip-coating over at least a part of the coagulant layer a layer of a first elastomer, c) immersing a first portion of the coated form into a solvent for the metallic ions of the metal salt to remove substantially all the metallic ions in the layers, d) dip coating a layer of a second elastomer over the first elastomeric layer, whereby the resultant elastomer coating is thinner on the first portion of the form than on the remainder of the coated form, and e) removing the coating from the form.

The process of the invention permits the fabrication of gloves having finger wall thickness of less than 0.13 mm, which makes these gloves well suited for ophthalmology, and other areas where the wearer of the glove must maintain maximum finger sensitivity. For brevity, we refer to gloves whose fingers have thinner walls than do their cuffs as "thin-fingered" gloves.

BRIEF DESCRIPTION OF THE DRAWINGS

FIG. 1 depicts a cross section of a tank with a glove form being coated over its "full" length.

FIG. 2 depicts the glove forms of FIG. 1 being dipped partially into the tank of FIG. 1.

FIG. 3 depicts the glove form of FIG. 1 being dipped partially into the tank of FIG. 1, to a different depth than is shown in FIG. 2.

FIG. 4 depicts a finished glove.

FIG. 5 is an enlarged cross section of part of the glove of FIG. 4.

DETAILED DESCRIPTION OF THE INVENTION

The present invention provides a method for fabricating medical gloves that have fingers whose wall thickness is very small. Medical professionals require thin-fingered gloves of that type in a number of medical situations, including ophthalmology and other exacting disciplines, in which only the minimum interference with the sensitivity of the bare hands can be tolerated. At the same time, these gloves must have sufficient strength—i.e., wall thickness—outside the finger area to permit the gloves to be donned and used conveniently and without significant risk of tearing. Since gloves are generally fabricated by dipping hand-shaped forms, fingers first, into a solution or dispersion of an elastomer. That fabrication procedure tends to yield gloves whose fingers have greater wall thickness than the rest of the glove, since the fingers of the form spend the longest time in the elastomer.

FIG. 1 illustrates part of an apparatus for practicing the present process. It is of a type that has long been used for making elastomeric gloves and includes a glove form 10, which generally has the shape of a hand, and a tank 12 into which the form is dipped. The complete apparatus includes a series of tanks, each similar to tank 12, into which the form is dipped successively. Of course, the liquid 14 would be different in the different tanks. For dipping purposes, the form 10, the tank 12, or both may be moved. When all the dipping steps are completed, a finished glove is removed, or "stripped", from the form and reversed so that the first layer is on the outside. The form 10 is generally made of glazed or bisque porcelain or plastic. Of course, the size of the form determines the size of the glove.

A variety of elastomers may be used for medical gloves, including natural rubber latex, nitrile rubber latex, coagulable polyurethane aqueous dispersion, and the like. In the present invention, the gloves are formed of two layers of elastomers, which may be different. A glove in which both layers are natural rubber latex is preferred, because it has superior properties and lower cost. For brevity and convenience, we will describe the process of this invention in the context of natural rubber latex gloves, recognizing that the modifications necessary to produce gloves of other common materials will be clear to the artisan. Conventional methods for preparing rubber latex gloves are described in a bulletin "Dipping With Natural Rubber Latex"; The Malaysian Rubber Producers' Research Association; Hertford, England, 1980, and the disclosure of that bulletin is incorporated herein by reference.

As was stated above, the conventional glove-manufacturing process yields gloves whose fingers have a greater wall thickness than their cuffs. To overcome this tendency and to provide gloves with thin fingers, the process of the present invention involves coagulant and multiple latex dips of a glove form, and extracting metallic ions—preferably, bivalent metallic ions—off the finger and thumb portions of the latex-coated glove form. The latex deposition rate on the area from which metallic ions have been extracted is substantially reduced during the second latex dip.

Glove forms are preferably heated to about 65°-75° C. before coating, in order to evaporate off any alcohol or water that may remain on the surface from a wash cycle. In order to provide reproducible latex layers on the form, a coagulant layer is first dipped onto the form. The coagulant may be of any composition well known in the art and described in the above-mentioned bulletin, such as aqueous or alcoholic solutions of calcium, or other metal, salts. The coagulant comprises a mold release agent, which facilitates removal of the finished glove from the form, and a bivalent metal salt, which causes a latex overcoat to gel. A preferred mold release agent and metallic salt are calcium carbonate and calcium nitrate, respectively.

The first latex dip determines the minimum wall thickness of the glove fingers. That thickness is less if the form is immersed in the latex for a shorter period of time, which, in turn, can be accomplished by limiting the first latex dip to a portion of the coagulant-coated glove form. The depth of the first latex dip may be at any position of the glove form. As shown in FIG. 2, however, the preferred depth of the first latex dip is just above the thumb crotch of the glove form. The first latex dip is a latex dispersion comprising elastomeric material(s), stabilizer(s), an antioxidant, an activator, a vulcanizer and accelerator(s). Preferably, the latex dispersion has lower solids percentage than is used for conventional glove production to facilitate achieving a thin coating. An alternative way of obtaining a thin coating with the first latex dip is to dip the bare glove mold in latex and to follow with the coagulant dip. That procedure is less preferred, however, because the finished glove, lacking the mold release agent in the first coating, is hard to strip from the mold.

In a coagulation dipping process, the film thickness deposited on a glove form increases with the metal ion concentration and the time the glove form spends immersed in the latex compound. Thus, latex deposition in the second dip is reduced on a portion of the coating by removing from that portion the metal ions, which diffuse from the coagulant layer to the surface of the latex deposited in the first dip. Metal ions are extracted from the coagulant latex deposit with water, alcohol, or a mixture of both. The preferred metal ion solvent is water. The temperature of the water is not critical and can be from as low as near the freezing point to near the boiling point, but room temperature or above is preferred; e.g., 68° F. (20° C.) to 150° F. (65° C.). The depth of the metal ion solvent determines the portion of the glove that will have thin walls and should not be greater than the depth of the first latex dip. The preferred depth is just above the finger crotches, as is illustrated in FIG. 3.

The amount of metallic ions extracted depends upon the concentration of metallic ions in the latex gel, salt content and temperature of the water, and time of contact with the water. Generally, the period of contact will be between a few seconds and 30 minutes, preferably a minute or two. While the contact time can be up to an hour or more, the extraction efficiency decreases markedly after about a half hour.

The second latex dip is applied to the full length of the glove form (as shown in FIG. 1). The latex formulation for the second latex dip can be the same as or different from the first latex dip. It is preferred that the second latex dip be a layer which can supply bulk, softness, strength and other physical properties to the glove. Based on these conditions, a natural rubber latex is a preferred material.

The process described above produces a thin-fingered glove (as defined earlier). FIG. 4 depicts the appearance of a finished glove. FIG. 5 depicts an enlarged cross section of a glove of the invention showing both the "thick" and "thin" regions. Wall thickness in the (thin) fingers is preferably less than about 0.13 mm.

For a better understanding of the present invention, the following examples illustrate various processes for producing thin-fingered gloves. The examples are not intended to be in any way limiting.

EXAMPLE I

A glove form having the general contour of a human hand is first heated in an oven. Then:

1. The heated glove form is dipped full length in a coagulant that comprises 20% calcium nitrate, 6% calcium carbonate and 0.5% wetting agent in an alcoholic solution.

2. A latex dip is applied up to just above the thumb crotch of the coagulant-coated glove form. The rubber compound for the first latex dip is a natural rubber latex compound having 28% solids.

3. The thumb and finger portions of the latex-coated glove form is immersed in a water bath at 126° F. (52° C.) for 1.5 minutes to extract calcium ions from the latex deposit. (Latex deposition on the portion immersed inside the hot water will, therefore, be minimal during the second latex dip.)

4. Excess water droplets are dried in a 230° F. (110° C.) oven for 3 minutes.

5. A second latex dip is applied to the full length of the reheated glove form. The rubber compound for the second latex dip is a natural rubber latex compound having 33% solids.

After the second latex deposit is gelled, it is leached with water, dried, vulcanized and stripped from the glove form to provide the finished glove.

EXAMPLE II

A form is first heated in an oven. Then:

1. A latex dip is applied to the full length of the heated glove form. The rubber compound for the first latex dip is a nitrile or a natural rubber latex compound having 40% solids.

2. The latex coated glove form is dipped full length in a coagulant that comprises 20% calcium nitrate and 0.5% wetting agent in an alcoholic solution.

3. The coagulant is washed off the thumb and finger portions of the coagulant coated glove form with the water at 126° F. (52° C.) for 1.5 minutes.

4. Excess water droplets are dried in a 230° F. oven for 3 minutes.

5. A second latex dip is applied to the full length of the reheated glove form. The rubber compound for the second latex dip is a natural rubber latex compound having 33% solids.

After the latex deposit is gelled, it is leached with water, dried, vulcanized and stripped from the glove form to provide the finished glove.

EXAMPLE III

In accordance with the general procedure of EXAMPLE II, a glove is formed utilizing NeoRex R-967, a polyurethane aqueous dispersion, for the first latex dip.

It is found that the finger gauge is less than the cuff gauge for gloves produced in accordance with EXAMPLE I, II or III.

I claim:

1. A process for making a medical glove comprising the steps of:
   a) dip-coating onto a glove form a layer of coagulant that comprises an ionic metal salt,
   b) dip-coating over at least a part of the coagulant layer a layer of a first elastomer, the thickness of the elastomer layer being less than about 0.13 mm,
   c) immersing a first portion of the coagulant- and elastomer-coated form into a solvent for the metallic ions of the metal salt to remove essentially all the metallic ions in the layers,
   d) dip coating a layer of a second elastomer over the first elastomeric layer, whereby essentially no elastomer deposits on the first portion of the form and the resultant elastomer coating is thinner on the first portion of the form than on the remainder of the coated form, and
   e) removing the coating from the form.

2. The process of claim 1, in which the ionic metal salt is a salt of a bivalent metal.

3. The process of claim 2, in which the metal salt is a calcium salt.

4. The process of claim 3, in which the metal salt is calcium nitrate.

5. The process of claim 1, in which the first and second elastomers comprise the same material.

6. The process of claim 5, in which the elastomer is natural rubber latex.

7. The process of claim 1, in which the solvent for the metallic ions is selected from the group consisting of water, alcohol, and mixtures thereof.

8. The process of claim 7, in which the solvent is water at a temperature above about 20° C.

9. The process of claim 1, in which the first elastomeric layer is coated over an area of the form that is less than that over which the coagulant is coated.

* * * * *